US006846891B2

(12) United States Patent
Petereit et al.

(10) Patent No.: US 6,846,891 B2
(45) Date of Patent: Jan. 25, 2005

(54) COATING AND BINDING AGENT FOR ORAL OR DERMAL PHARMACEUTICAL FORMS

(75) Inventors: Hans-Ulrich Petereit, Darmstadt (DE); Christian Meier, Darmstadt (DE); Erna Roth, Darmstadt (DE)

(73) Assignee: Roehm GmbH & Co. KG, Darmstadt (DE)

( * ) Notice: Subject to any disclaimer, the term of this patent is extended or adjusted under 35 U.S.C. 154(b) by 0 days.

(21) Appl. No.: 10/463,539

(22) Filed: Jun. 18, 2003

(65) Prior Publication Data

US 2003/0220413 A1 Nov. 27, 2003

Related U.S. Application Data

(62) Division of application No. 09/764,993, filed as application No. PCT/EP99/04620 on Jul. 2, 1999, now Pat. No. 6,624,210.

(30) Foreign Application Priority Data

Jul. 23, 1998 (DE) .......................... 198 33 016
Apr. 23, 1999 (DE) .......................... 199 18 435

(51) Int. Cl.$^7$ ............................................. C08F 220/52
(52) U.S. Cl. ................. 526/303.1; 526/307.7; 524/555; 524/904
(58) Field of Search ................... 526/307.7, 318.6, 526/303.1; 524/555, 904

(56) References Cited

U.S. PATENT DOCUMENTS

| | | |
|---|---|---|
| 4,071,653 A | 1/1978 | Boessler et al. |
| 4,433,076 A | 2/1984 | Bauer et al. |
| 4,705,695 A | 11/1987 | Lehmann et al. ............... 427/3 |
| 5,025,004 A | 6/1991 | Wu et al. .................... 514/165 |
| 5,292,522 A | 3/1994 | Petereit et al. ............... 424/490 |
| 5,730,999 A | 3/1998 | Lehmann et al. ........... 424/443 |
| 6,034,183 A * | 3/2000 | Okumura et al. ........... 525/293 |
| 6,153,220 A * | 11/2000 | Cumming et al. .......... 424/464 |
| 6,391,338 B1 * | 5/2002 | Frisbee et al. .............. 424/487 |

FOREIGN PATENT DOCUMENTS

EP    0 727 205    8/1996

\* cited by examiner

Primary Examiner—Tae H. Yoon
(74) Attorney, Agent, or Firm—Oblon, Spivak, McClelland, Maier & Neustadt, P.C.

(57) ABSTRACT

The invention relates to a method for the production of a coating and excipient agent for oral or dermal dosage forms, consisting of (a) 35–98% by weight of a copolymer consisting of radically polymerized C1–C4 esters of acrylic or methacrylic acid and additional (meth)acrylate monomers having functional tertiary amino groups and (b) 1–50% by weight of a softener and 1–15% by weight of an emulgator with an HLB value of less than 14, wherein constituents (a), (b) and (c) are mixed with or without adding water and optionally adding a pharmaceutical active substance and other conventional additives and the coating and excipient agent is produced by melting, casing, spreading or spraying. The invention is characterized in that the copolymer (a) is applied in powder form with a mean particle size of 1–40 μm.

2 Claims, No Drawings

COATING AND BINDING AGENT FOR ORAL OR DERMAL PHARMACEUTICAL FORMS

This application is a Division of application Ser. No. 09/764,993 filed on Jan. 23, 2001, now U.S. Pat. No. 6,624,210, issued Sep. 23, 2003, which is the National Stage of International Application No. PCT/EP99/04620, filed Jul. 2, 1999.

The invention relates to a coating and binding agent for oral and dermal pharmaceutical forms, comprising a (meth) acrylate copolymer, plasticizer and emulsifier.

PRIOR ART

The use of (meth)acrylate copolymers in pharmaceutical coatings has been known for decades. (Meth)acrylate copolymers containing monomer units with tertiary amino groups are suitable, for example, for pharmaceutical coatings which mask the taste and which dissolve in the gastric fluid and thus permit rapid release of active principle. Such polymers can be processed very effectively in the form of organic solutions. Unfortunately organic solvents suffer from several disadvantages, in that, for example, they pollute the environment and are toxic and readily flammable. Thus efforts already began years ago, wherever possible, to replace organic solutions by aqueous dispersions or to permit processing without any addition of solvent whatsoever (such as processing in the melt).

U.S. Pat. No. 4,705,695 describes a process for coating pharmaceutical formulations with an aqueous coating agent containing a water-soluble (meth)acrylate copolymer with tertiary amino groups as well as a water-insoluble, neutral polymer as binder. The solubility of the (meth)acrylate copolymer comprising, for example, equal proportions of methyl methacrylate and dimethylaminoethyl methacrylate is achieved by stirring the powder form with particle sizes smaller than 0.25 mm into water while simultaneously adding an acid. As the binder there is used an insoluble copolymer comprising, for example, methyl methacrylate and ethyl acrylate (70:30). The preparation of the coating solution is relatively complex. Because of the acid content, the coating has an unpleasant taste. Corresponding films dissolve both in synthetic gastric fluid as well as in water in less than two minutes.

European Patent 181515 B describes a process for preparation of an aqueous coating agent dispersion and the use thereof for coating of pharmaceuticals. For this purpose there is used a (meth)acrylate copolymer containing quaternary ammonium groups, which copolymer swells but is not soluble in water. The copolymer can comprise, for example, methyl methacrylate, ethyl acrylate and 2-trimethylammonium ethyl methacrylate chloride (60:30:10). It is preferably used in the form of finely ground powder in the particle-size range smaller than 200 μm. Particle sizes smaller than 20 to 50 μm can be used, but are less suitable because of the dust generation tendency. The powder dissolves in water at elevated temperature after prolonged stirring. Dispersion is promoted by the addition of plasticizers. Addition of emulsifiers is said to be unnecessary.

European Patent Application 0727205 A describes thermoplastically processable coating and binding agents for pharmaceutical forms. Therein there is described among other possibilities the solvent-free processing to meltable pharmaceutical formulations of (meth)acrylate copolymers containing monomer units with tertiary amino groups, by means of addition of incompatible fluidizing agents such as glycol monostearate.

OBJECT AND ACHIEVEMENT

In contrast to (meth)acrylate copolymers containing monomer units with quaternary amino groups, heretofore it has not been possible, without addition of acids, to convert to stable aqueous solutions or dispersions (meth)acrylate copolymers which contain monomer units with tertiary amino groups. In addition, further additives such as neutral (meth)acrylate copolymers are usually necessary in order to obtain formulations that can be sprayed at all.

Coatings according to U.S. Pat. No. 4,705,695 cited in the introduction also have the disadvantage that they are expensive to prepare, have a bitter taste and can be prepared only by relatively complex means. Since such formulations already dissolve rapidly in pure water, they are unsuitable as taste-masking coatings.

One object of the present invention was seen as providing a formulation and a process for preparation of a coating and binding agent for pharmaceutical forms containing (meth) acrylate copolymers with monomer units with tertiary amino groups, which process permits simple wet or dry further processing. In this connection the formulations should be suitable in particular for preparation of taste-masking coatings and therefore should be less soluble in water than in synthetic gastric fluid. The aqueous formulations should be readily processable, especially by spray application. Furthermore, the formulations should also be suitable for dry processing, in order to provide a further alternative to the meltable pharmaceutical formulations according to European Patent Application 0727205 A.

Surprisingly it has been found that the object is achieved by a process for preparation of a coating and binding agent for oral or dermal pharmaceutical forms comprising
  (a) 35 to 98 wt % of a copolymer comprising radical-polymerized C1 to C4 esters of acrylic or methacrylic acid and further (meth)acrylate monomers containing functional tertiary amino groups and
  (b) 1 to 50 wt % of a plasticizer as well as
  (c) 1 to 15 wt % of an emulsifier with an HLB value of at least 14,
wherein components (a), (b) and (c) are intermixed with each other with or without addition of water and possibly with addition of a pharmaceutical active principle and further common fillers, and the coating and binding agent is prepared by melting, casting, doctoring or spraying, characterized in that
  the copolymer (a) is introduced in powder form with a mean particle size of 1 to 40 μm.

The surprisingly good processability of the formulation is due to the provision of copolymer (a) in powder form with extremely small particle size, and was not foreseeable. Copolymer (a) in this powder form is new and is also claimed. Furthermore, the invention is based on the knowledge that components (a), (b) and (c) must be present in well-defined ratios in order to achieve the stated object. It is assumed that the advantageous effects are due to mutual interactions of the components with each other during the preparation process. The coating and binding agents which are also part of the invention are therefore characterized by the preparation process.

Since the advantageous effects are also achieved without use of water or solvents, the components can also be processed in dry form. It is suspected that under these conditions constituents (a) and (b) and (c) aggregate with each other in advantageous manner under the effect of heat.

The layers or coatings that can be prepared from the powder are insoluble or difficultly soluble in water. The layer transformed to film remains impervious in the neutral environment of the mouth, but in synthetic gastric fluid it dissolves rapidly and releases the encapsulated or embedded active principle very rapidly in the desired manner.

OPERATION OF THE INVENTION

Component (a)

Copolymers (a) comprise substantially or completely radical-polymerized C1 to C4 esters of acrylic or methacrylic acid and further (meth)acrylate monomers containing functional tertiary amino groups.

Suitable monomers with functional tertiary amino groups are listed in U.S. Pat. No. 4,705,695, column 3, line 64 to column 4, line 13. Worth special mention are dimethylaminoethyl acrylate, 2-dimethylaminopropyl acrylate, dimethylaminopropyl methacrylate, dimethylaminobenzyl acrylate, dimethylaminobenzyl methacrylate, (3-dimethylamino-2,2-dimethyl)propyl acrylate, dimethylamino-2,2-dimethyl) propyl methacrylate, (3-diethylamino-2,2-dimethyl)propyl acrylate and diethylamino-2,2-dimethyl)propyl methacrylate. Especially preferred is dimethylaminoethyl methacrylate.

The content of monomers with tertiary amino groups in the copolymer can range advantageously between 30 and 70 wt %, preferably between 40 and 60 wt %. The proportion of the C1 to C4 esters of acrylic or methacrylic acid is 70 to 30 wt %. Examples of such esters are methyl methacrylate, ethyl methacrylate, butyl methacrylate, methyl acrylate, ethyl acrylate, butyl acrylate.

A (meth)acrylate copolymer with tertiary amino groups, corresponding to component (a), can be composed, for example, from 20 to 30 wt % of methyl methacrylate, 20 to 30 wt % of butyl methacrylate and 60 to 40 wt % of dimethylaminoethyl methacrylate.

The proportion of component (a) in the formulation is 35 to 98 wt %, preferably 60 to 90 wt %.

Copolymers (a) are obtained in a manner known in itself by radical, bulk, solution, bead or emulsion polymerization. Before processing they must be transformed into the inventive particle-size range by appropriate grinding, drying or spraying processes. Suitable apparatus for preparation of the powders are familiar to those skilled in the art. Examples are air-jet mills, pinned-disk mills, fan mills. If necessary, appropriate sieving steps can be included. A suitable mill for industrial large quantities is, for example, a counterjet mill (Multi No. 4200), which is operated with a gauge pressure of about 6 bar.

The mean particle size of the powders can be determined as follows:

By air-jet screening for simple separation of the ground product into a few fractions. In the present measurement range, this method is somewhat less accurate than the alternatives. At least 70% and preferably 90% of the particles relative to the weight (weight distribution), however, must lie within the inventive size range of 1 to 40 $\mu$m.

A highly suitable measuring method is laser refraction for determination of particle-size distribution. Commercial instruments permit measurement in air (Malvern Co. S3.01 Particle Sizer) or preferably in liquid media (LOT Co., Galai CIS 1). The prerequisite for measurement in liquids is that the polymer does not dissolve therein or the particles do not change in some other way during the measurement. An example of a suitable medium is a highly diluted (about 0.02%) aqueous Polysorbate 80 solution. The mean particle diameter must range between 1 and 40, preferably between 5 and 35, especially between 10 and 20 $\mu$m.

Component (b)

Plasticizers can influence the functionality of the polymer layer depending on type (lipophilic or hydrophilic) and added proportion. Plasticizers achieve lowering of the glass transition temperature by physical interaction with the polymers and promote film formation as a function of the added proportion. Suitable substances usually have a molecular weight of between 100 and 20,000 and contain one or more hydrophilic groups such as hydroxyl, ester or amino groups in the molecule.

Examples of suitable plasticizers are citric acid alkyl esters, glycerol esters, phthalic acid alkyl esters, sebacic acid alkyl esters, sucrose esters, sorbitan esters, dibutyl sebacate and polyethylene glycols 200 to 12,000. Preferred plasticizers are triethyl citrate (TEC), acetyl triethyl citrate (ATEC) and dibutyl sebacate (DBS). Others worth mentioning are esters that are usually liquid at room temperature, such as citrates, phthalates, sebacates or castor oil. Preferably there are used citric acid and sebacic acid esters.

The addition of plasticizer (b) to the formulation can be accomplished in known manner, directly, in aqueous solution or after heat pretreatment of the mixture. Mixtures of plasticizers can also be used.

The proportion of component (b) in the formulation is 1 to 50, preferably 5 to 30 wt %.

Component (c)

Emulsifiers or surfactants are interfacially active substances with lyobipolar character, meaning that nonpolar, lipophilic centers as well as polar, hydrophilic centers must be present in their molecule (P.H. List, The Science of Pharmaceutical Forms, Wissenschaftliche Verlagsgesellschaft mbH Stuttgart, 1982, Chapter 6.2). Depending on molecular structure, a distinction is made between ionogenic and nonionogenic emulsifiers.

The HLB value is a concept introduced by Griffin in 1950 as a measure of the hydrophilicity or lipophilicity of nonionic surfactants. It can be determined experimentally by the phenol titration method of Marszall; see "Parfümerie, Kosmetik", Vol. 60, 1979, pp. 444–448; further literature references can be found in Römpp, Chemistry Lexicon, 8th Edition 1983, p. 1750. See also, for example, U.S. Pat. No. 4,795,643 (Seth).

An HLB value (hydrophilic/lipophilic balance) can be determined exactly only for nonionic emulsifiers. In the case of anionic emulsifiers this value can be determined theoretically, but it is almost always higher or much higher than 14.

According to the invention, emulsifiers (c) with an HLB value above 14 are to be understood as hydrophilic, nonionic emulsifiers with an HLB range of at least 14 as well as anionic emulsifiers, which are also hydrophilic, and salts thereof that have a theoretical HLB value above 14. Certainly emulsifiers with HLB values of less than 14, such as glycerol monostearate, can also be present in addition, but they do not replace the emulsifiers (c) with HLB values of at least 14.

Examples of suitable emulsifiers (c) are sodium lauryl sulfate and sodium cetyl stearyl sulfate, sucrose stearate and Polysorbate 80. Emulsifiers (c) are present in proportions of 1 to 15, preferably 5 to 10 wt %. Naturally the use of emulsifier mixtures is also possible.

The addition of emulsifiers (c) to the formulation can be accomplished in known manner, directly in aqueous solution or after heat pretreatment of the mixture.

Emulsifiers can influence the functionality of the polymer layer depending on type and added proportion.

Further Fillers

Standard fillers are usually added to the inventive formulation during processing to coating and binding agents.

The quantities introduced and the use of standard fillers in pharmaceutical coatings or overlayers are familiar to those skilled in the art. Examples of standard fillers are release agents, pigments, stabilizers, antioxidants, pore-forming agents, penetration-promoting agents, brighteners, fragrances or flavoring agents. They are used as processing adjuvants and are intended to ensure a reliable and reproducible preparation process as well as good long-term storage stability, or they achieve additional advantageous properties in the pharmaceutical form. They are added to the polymer formulations before processing and can influence the permeability of the coatings. This property can be used if necessary as an additional control parameter.

Release Agents

Release agents usually have lipophilic properties and are usually added to spray suspensions. They prevent agglomeration of cores during film formation. There are preferably used talc, Mg or Ca stearate, ground silica, kaolin or nonionic emulsifiers with an HLB value of between 3 and 8. Standard proportions for use of release agents in the inventive coating and binding agents range between 0.5 and 100 wt % relative to copolymer (a).

In a particularly advantageous embodiment, the release agent is added in concentrated form as the outer layer. Application takes place in the form of powder or by spraying from aqueous suspension with 5 to 30% solid content. The necessary concentration is lower than for incorporation into the polymer layer and amounts to 0.1 to 2% relative to the weight of the pharmaceutical form.

Pigments

Only rarely is the pigment added in soluble form. As a rule, aluminum oxide or iron oxide pigments are used in dispersed form. Titanium dioxide is used as a whitening pigment. Standard proportions for use of pigments in the inventive coating and binding agents range between 20 and 60 wt % relative to the polymer mixture. Because of the high pigment-binding capacity, however, proportions as high as 100 wt % can also be processed.

In a particularly advantageous embodiment, the pigment is used directly in concentrated form as the outer layer. Application takes place in the form of powder or by spraying from aqueous suspension with 5 to 30% solid content. The necessary concentration is lower than for incorporation into the polymer layer and amounts to 0.1 to 2% relative to the weight of the pharmaceutical form.

In principle, all substances used must of course be toxicologically safe and be used in pharmaceuticals without risk for patients.

The Preparation Process

Components (a), (b) and (c) are intermixed with each other with or without addition of water and if necessary with addition of a pharmaceutical active principle and further common fillers, and the coating and binding agent is prepared by melting, casting, doctoring or spraying. In this connection transformation of the coating to a film and binding agent is the prerequisite for the functional effect in pharmaceutical forms.

Transformation to film takes place by input of energy, regardless of the application process. This can be accomplished by convection (heat), radiation (infrared or microwave) or conduction. Water used as suspension agent for application then evaporates. If necessary, a vacuum can also be employed to accelerate evaporation. The temperature required for transformation to film depends on the combination of components used.

Use of the Inventive Formulation for Preparation of Binding Agents

The use as binding agents is carried out, for example, by spraying the aqueous polymer suspension of cores free of active principle (nonpareils) with simultaneous addition of powdered active principles or mixtures thereof. A further embodiment comprises spraying of the aqueous polymer suspension together with active principles dissolved or suspended therein.

Use of the Inventive Formulation for Preparation of Coating Agents

Substrates for coatings are capsules, tablets, granules, pellets and crystals of regular or irregular shape. The size of granules, pellets or crystals ranges between 0.01 and 2.5 mm, and that of tablets between 2.5 and 30.0 mm. Capsules are made of gelatins, starches or cellulose derivatives.

They usually contain up to 95% of the biologically active substance (active principle) as well as up to 99.9 wt % of further pharmaceutical adjuvants. Standard manufacturing processes are direct pressing, pressing of dry, moist or sintered granules, extrusion followed by forming to rounded shape, moist or dry granulation or direct pelleting (on plates, for example) or by binding of powders (powder layering) on spherules free of active principle (nonpareils) or on particles containing active principle.

Besides the active principle they can contain further pharmaceutical adjuvants: binders such as cellulose and derivatives thereof, polyvinylpyrrolidone (PVP), humectants, disintegration promoters, lubricants, blasting agents, (meth)acrylates, starches and derivatives thereof, sugar, solubilizers or other substances.

Of special importance is the disintegration time of the cores, which influences the release of the active principle. Current practice is to aim for short disintegration times of less than 5 or less than 10 minutes in the disintegration test per the European Pharmacopoeia. Longer disintegration times are problematic, because additional coatings further retard release of the active principle and can jeopardize the therapeutic effect. A disintegration time of 30 minutes is now regarded as the limit value. The property is tested in water and synthetic gastric fluid (0.1 N HCl). As regards the function of polymers containing tertiary amino groups, the influence of pH on disintegration of the cores or release of active principle is important. Adequate functionality is achieved if the disintegration time in water is at least twice as long as in synthetic gastric fluid.

The cores used are homogeneous or have a layered structure. If splitting lines are sunk into the surfaces, they should be covered as well as possible but only slightly filled by coatings. The layer thickness of polymer powder used according to the invention varies greatly and depends on the processing method or on the quantity of fillers. It ranges between 1 and 100 $\mu$m, preferably between 10 and 50 $\mu$m. On standard tablets this corresponds to a polymer application of 0.5 to 5 wt %. According to K. Lehmann et al., Drugs made in Germany 37, 2, 53–60 (1994) and T. E. Beckert et al., International Journal of Pharmaceutics 143 (1996), 13–23, coated microparticles can be pressed to disintegrating tablets without significant influence on the function of the polymer.

The function of the polymer layer transformed to film in the final pharmaceutical form can be diverse:

protection against harmful environmental influences due to humidity, gases, light, etc.

masking smell or taste, identification by color mechanical stabilization isolation of incompatible adjuvants prevention of adherence to the mucous membranes timed release of active principles pH-controlled release of active principles An advantage is the low viscosity of the polymer mixture in aqueous dispersion even at high solid contents of up to 30%, since splitting lines on the surface of tablets can be patterned in detail. Particularly advantageous is the good protective and masking effect of the inventive polymer mixture with simultaneously slight influence on tablet disintegration. Even in the case of small polymer applications of 1 wt %, taste masking for longer than 30 seconds is already achieved. Thicker coatings with a copolymer of methyl methacrylate, butyl methacrylate and dimethylaminoethyl methacrylate in proportions of 25:25:50 (EUDRAGIT® E 100) improve the taste masking without prolonging the disintegration time in 0.1 N HCl. Also advantageous is the reliable covering of colored cores by coatings with high proportion of pigment. A special embodiment comprises the embedding of a second active principle in the coating on a core containing active principle.

Application on the Inventive Formulation for Preparation on Substrates

The inventive formulation can be used in powder form, as a melt or in aqueous suspension by casting, doctoring or by means of spray application. For this purpose water is mainly used as the vehicle, in order to apply thin encapsulations uniformly on spherical cores, for example by spraying. Doctoring processes are also used for forming layers. The process used depends mainly on the selected substrate. Dry powder is applied by doctoring or dusting, if necessary by also using electrostatic forces. The deciding factor for operation is that uniform, continuous layers are produced.

Application processes of the prior art can be found in, for example, Bauer, Lehmann, Osterwald, Rothgang, "Coated Pharmaceutical Forms, Wissenschaftliche Verlagsgesellschaft mbH Stuttgart, Chapter 7, pp. 165–196. Properties relevant for application as well as required tests and specifications are listed in pharmacopoeias. Details can be found in common textbooks, such as:

Voight, R. (1984): Textbook of Pharmaceutical Technology; Verlag Chemie Weinheim—Beerfield Beach/Fla.—Basel.

Sucker, H., Fuchs, P., Speiser, P.: Pharmaceutical Technology, Georg Thieme Verlag Stuttgart (1991), especially Chapters 15 and 16, pp. 626–642.

Gennaro, A. R. (Editor), Remington's Pharmaceutical Sciences, Mack Publishing Co., Easton Pa. (1985), Chapter 88, pp. 1567–1573.

List, P. H. (1982): The Science of Pharmaceutical Forms, Wissenschaftliche Verlagsgesellschaft mbH, Stuttgart.

The inventive coating and binding agents can be used as constituents of a transdermal therapy system. The typical case for this purpose is an adhesive bandage, which contains a pharmaceutical active principle which, after release, acts topically or is absorbed through the skin into the bloodstream and distributed in the body, where it acts systemically.

Dermal and transdermal therapy systems often have a multilayer structure and, on the basis of the structural composition, are divided into:

reservoir systems matrix systems drug-in-adhesive systems multi-laminate systems This pharmaceutical is embedded in one or more layers of these systems and, after fixation on the skin, is released at a controlled rate in order to develop the desired effect.

The following active principles (or salts thereof) are already contained in commercial preparations or are undergoing development: nicotine, nitroglycerin, scopolamine, clonidine, fentanyl, estradiol, testosterone, oxybutynin, diclophenac, ibuprofen, ketoprofen, diltiazem, propranolol, albuterol, alprazolam, amethocaine, atenolol, benzoporphyrin, buprenorphine, calcitonin, dithranol, diphencyprone, diverse peptides, eptazocines, ethinyl estradiol, methotrexate, naloxone and tretinion.

In a special embodiment, a layer of antiadhesive substrates is applied and the inventive coating and binding agent is transformed to a film. Then the obtained film is separated from the substrate and used in free form for lamination, calendering or encapsulation. The necessary adhesion is achieved by heating, adhesive bonding. In the process, pressure can additionally be used for stabilization.

Biologically Active Substances

The pharmaceuticals used within the meaning of the invention are designed for administration in the human or animal body in order 1. to cure, alleviate, prevent or detect diseases, injuries, body damage or pathological conditions,
2. to allow the nature, condition or functions of the body or mental conditions to be discerned,
3. to replace active principles or body fluids generated by the human or animal body,
4. to combat, eliminate or render harmless pathogens, parasites or substances foreign to the body or
5. to influence the nature, condition or functions of the body or mental conditions.

Common pharmaceuticals can be found in reference works such as the Red List or the Merck Index. According to the invention there can be used all active principles that satisfy the therapeutic effect within the meaning of the definition given hereinabove and that have adequate thermal stability.

Without claiming completeness, important examples (groups and individual substances) are the following:

analgesics, antiallergics, antiarrhythmics antibiotics, chemotherapeutics, antidiabetics, antidotes, antiepileptics, antihypertensives, antihypotensives, anticoagulants, antimycotics, antiphlogistics, beta receptor blockers, calcium antagonists and ACE inhibitors, broncholytics/antiasthmatics, cholinergics, corticosteroids (internal), dermatics, diuretics, enzyme inhibitors, enzyme preparations and transport proteins, expectorants, geriatrics, gout remedies, flu medicines, hormones and their inhibitors, hypnotics/sedatives, cardiacs, lipid-lowering drugs, parathyroid hormones/calcium metabolism regulators, psychopharmaceuticals, sex hormones and their inhibitors, spasmolytics, sympatholytics, sympathomimetics, vitamins, wound medications, cytostatics.

Preferred active principles for slow release of active principles are:

nifedipine, diltiazem, theophylline, diclofenac sodium, ketoprofen, ibuprofen, indomethacin, ambroxol, terbutaline, vincamine, propranolol, pentoxifylline, codeine, morphine, etilefrin, carbamazepine or the therapeutically used salts thereof.

Application Forms

In principle the described pharmaceutical forms can be administered directly by oral application. The granules, pellets or particles prepared according to the invention can be filled into gelatin capsules, bags (sachets) or appropriate multi-dose containers with dispensing device. Ingestion takes place in solid form or as a suspension in liquids. By pressing there are obtained, if necessary after mixing in further adjuvants, tablets that disintegrate after ingestion and usually release coated subunits. Also conceivable is the embedding of agglomerates in polyethylene glycol or lipids for preparation of suppositories or vaginal pharmaceutical forms. Coated tablets are packed in blisters or multi-dose containers and are removed by the patient just before ingestion.

EXAMPLES

The formulations and galenic data of the tablets used in the examples are described in the following table:

| Constituents | Placebo tablets | Quinidine sulfate tablets | Methylene Blue tablets |
|---|---|---|---|
| Cellactose ® | — | 92.5% | |
| Avicel ® PH 102 | 30.0% | 5.0% | 30.0% |
| Mg stearate | 0.3% | 0.5% | 0.3% |
| Quinidine sulfate | — | 2.0% | |
| Lactose D 20 | 61.2% | — | 59.2% |
| Aerosil 200 | 0.5% | — | 0.5% |
| Talc | 3.0% | — | 3.0% |
| Amijel | 5.0% | — | 5.0% |
| Methylene Blue | | | 2.0% |
| Appearance | white | white | white-blue |
| Diameter | 8.0 mm | 10.0 mm | 7.0 mm |
| Height | 3.95 mm | 3.91 mm | 4.06 |
| Weight | 191 to 210 mg | 398 to 312 mg | 142 mg |
| Hardness | 93 to 102 N | 113 to 133 N | >50 N |
| Disintegration in demineralized water | 15 to 40 sec | 13 to 20 min | 15 to 60 sec |
| Disintegration in 0.1 N HCl | 15 to 42 sec | 14 to 20 min | 10 to 37 sec |

All adjuvants used have pharmaceutical quality. The preparation of the aqueous suspension of glycerol monostearate (GMS) used in some examples and accomplished by suspension of GMS in an appropriate volume of water, heating to about 60° C. and cooling the batch to room temperature while homogenizing with a high-speed mixer (such as Ultra Turrax).

The powder from copolymer (a) of methyl methacrylate, butyl methacrylate and dimethylaminoethyl methacrylate in proportions of 25:25:50 (EUDRAGIT® E100) was prepared by grinding of the extruded granules in various air-jet mills (inventive particle sizes) or a pinned-disk mill (not inventive particle size).

The particle sizes were determined in an S3.01 Particle Sizer (Malvern Instruments Co.) or in a Galai CIS 1 (LOT Co.).

Examples 1 to 3 Describe the Direct Application of the Inventive Coating and Binding Agent as a Powder or Paste In Examples 4 to 17 there are Described Alternative Formulations and Embodiments in the Form of Aqueous Suspensions Examples 18 to 20 Describe Embodiments that are not in Accordance with the Invention (Comparison Examples)

1. Preparation of a Masking Layer with a Hydrophilic Plasticizer and a Nonionic Emulsifier 3.5 g of a copolymer of methyl methacrylate, butyl methacrylate and dimethylaminoethyl methacrylate in proportions of 25:25:50 (EUDRAGIT® E 100) was mixed in the mortar with 5 g of polyethylene glycol 12000 plus 1.5 g of sucrose stearate. The obtained powder was doctored uniformly onto Teflon sheet and transformed to a film in a drying oven at 100° C. for about 15 hours. There was formed a cohesive clear film, which does not dissolve in demineralized water. It can be transferred by the transfer process, for example, onto flat substrates or can be used as free film for encapsulation of cubic cores. In the process, individual layers can be adhesively bonded or heat-sealed to one another.

2. Preparation of a Masking Layer with a Hydrophilic Plasticizer and a Nonionic Emulsifier In a mortar there were mixed 10.0 g of a copolymer of methyl methacrylate, butyl methacrylate and dimethylaminoethyl methacrylate in proportions of 25:25:50 (mean particle size 10 μm), 5 g of TEC and 1.5 g of Polysorbate 80. This milky white, highly viscous paste was doctored onto a Teflon-coated glass plate and transformed to a film as in Example 1. There was formed a clear, tacky film, which is insoluble in demineralized water and can be used as in Example 1.

3. Preparation of a Masking Layer with a Lipophilic Plasticizer and a Nonionic Emulsifier In a mortar there were mixed 5 g of dibutyl sebacate, 1.5 g of sucrose stearate and 5 g of a copolymer of methyl methacrylate, butyl methacrylate and dimethylaminoethyl methacrylate in proportions of 25:25:50 (mean particle size 10 μm). This milky white, highly viscous paste was doctored onto a Teflon-coated glass plate and transformed to a film as in Example 1. There was formed a clear, tacky film, which is insoluble in demineralized water and can be used as in Example 1.

4. Colorless Masking Coating with a Nonionic Emulsifier and a Hydrophilic Plasticizer In a glass beaker there were mixed by means of a paddle stirrer 274 g of water, 18 g of a 33.3% Polysorbate solution and 9 g of triethyl citrate. Then 60 g of a copolymer of methyl methacrylate, butyl methacrylate and dimethylaminoethyl methacrylate in proportions of 25:25:50 (mean particle size 15.3 μm) was added slowly with stirring, after which stirring was continued for a further 90 minutes.

Now 20 g of a 6% glycerol monostearate suspension was added to the mixture and homogenized for another 10 minutes at a speed of 3500 rpm using an Ultra Turrax.

The obtained spray suspension was sprayed onto 1500 g of placebo tablets in a sugar-coating pan (25 cm diameter, speed about 40 rpm) using a spray gun (spraying pressure 0.8 bar). The product temperature was kept at 25 to 40° C. and the water used was evaporated by passage of preheated air. The polymer application corresponded to 4 mg/cm$^2$. The spraying time was 60 minutes. Finally, 3 g of magnesium stearate was sprinkled and the product was dried overnight at room temperature. The tablets had a smooth glossy surface and, in the disintegration test per the European Pharmacopoeia, exhibited the following values in demineralized water and synthetic gastric fluid:

| | Polymer application | |
|---|---|---|
| | 4 mg/cm$^2$ | uncoated |
| Demineralized water | 15 to >20 min | 0.2 to 0.7 min |
| 0.1 N HCl | 0.3 to 1 min | 0.2 to 0.7 min |

5. Colorless Masking Coating with an Ionic Emulsifier and a Lipophilic Plasticizer In a glass beaker there were placed 30.0 g of a copolymer of methyl methacrylate, butyl methacrylate and dimethylaminoethyl methacrylate in proportions of 25:25:50 (mean particle size 13.3 $\mu$m) and 3.0 g of sodium lauryl sulfate, 150 g of demineralized water, then 6 g of dibutyl sebacate was mixed in and stirred for 1.5 hours. Then 20 g of talc and 80 g of demineralized water were added to the suspension, after which stirring was continued for a further 10 minutes. The obtained spray suspension was applied on placebo tablets as described in Example 4. The total polymer application corresponded to 2 mg/cm². The spraying time was 71 minutes. Then the product was dried overnight at room temperature. The tablets had a glossy uniform coating and, in the disintegration test per the European Pharmacopoeia, exhibited the following values in demineralized water and synthetic gastric fluid:

|  | Polymer application | | |
| --- | --- | --- | --- |
| Medium | 1 mg/cm² | 2 mg/cm² | uncoated |
| Demineralized water | 1.5 to 2 min | 1.5 to 2.3 min | 0.2 to 0.7 min |
| 0.1 N HCl | 1 min | 1 to 1.3 min | 0.2 to 0.7 min |

6. Colorless Masking Coating with an Ionic Emulsifier and a Lipophilic Plasticizer In a glass reactor there were placed 123.0 g of a copolymer of methyl methacrylate, butyl methacrylate and dimethylaminoethyl methacrylate in proportions of 25:25:50 plus 4.5 g of sodium lauryl sulfate and 600 g of demineralized water, and were stirred with the dissolver disk at a speed of 600 rpm under a vacuum of 720 mbar, heated to 45° C. and stirred at this temperature for 1.5 hours. Then 18.0 g of dibutyl sebacate was added slowly and the mixture cooled with stirring to 20° C. within 60 min. Now another 4.5 g of sodium lauryl sulfate was added and stirring was continued for up to a total of 5 hours. 183 g of this dispersion was mixed with 30 g of talc and 40 g of demineralized water in a glass beaker and stirred for about 20 minutes. The obtained spray suspension was applied on placebo tablets as described in Example 4. The total polymer application corresponded to 2 mg/cm². The spraying time was 46 minutes. Then the product was dried overnight at room temperature. The tablets had a uniform, glossy coating and, in the disintegration test per the European Pharmacopoeia, exhibited the following values in demineralized water and synthetic gastric fluid:

|  | Polymer application | | |
| --- | --- | --- | --- |
| Medium | 11 mg/cm² | 2 mg/cm² | uncoated |
| Demineralized water | 3.3 to 4.5 min | 4.5 to 6.5 min | 0.2 to 0.7 min |
| 0.1 N HCl | 0.7 to 1.2 min | 0.8 to 1.3 min | 0.2 to 0.7 min |

7. Colorless Masking Coating with an Ionic Emulsifier and a Lipophilic Plasticizer In a glass reactor, 131.8 g of an extruded and ground mixture (mean particle size 4.5 $\mu$m) of a copolymer of methyl methacrylate, butyl methacrylate and dimethylaminoethyl methacrylate in proportions of 25:25:50 plus glycerol monostearate (70/30), 7.3 g of sodium lauryl sulfate and 10.94 g of dibutyl sebacate in 600 g of demineralized water were dispersed with the dissolver disk for 5 hours at a speed of 400 rpm under a vacuum of 720 mbar at 30° C. The obtained spray suspension was applied on placebo tablets as described in Example 4. The polymer application corresponded to 2 mg/cm². The spraying time was 84 minutes. The tablets were dried overnight at room temperature. They had a uniform, glossy coating and, in the disintegration test per the European Pharmacopoeia, exhibited the following values in demineralized water and synthetic gastric fluid:

|  | Polymer application | | |
| --- | --- | --- | --- |
| Medium | 1 mg/cm² | 2 mg/cm² | uncoated |
| Demineralized water | 1.5 to 2.1 min | 2.1 to 3.0 min | 0.2 to 0.7 min |
| 0.1 N HCl | 0.7 to 1.0 min | 0.8 to 1.3 min | 0.2 to 0.7 min |

8. Colorless Masking Coating with an Ionic Emulsifier and a Lipophilic Plasticizer with Outer Coating In a glass beaker there was dissolved at 70° C. 6 g of sodium cetyl stearyl sulfate (Lanette E) in 288 g of demineralized water. Now 60 g of a copolymer of methyl methacrylate, butyl methacrylate and dimethylaminoethyl methacrylate in proportions of 25:25:50 (mean particle size 15.3 $\mu$m) plus 6 g of dibutyl sebacate were added slowly. Now stirring was continued for a further hour at this temperature on the heatable magnetic stirrer, after which the mixture was cooled to about 50° C., a further 3 g of dibutyl sebacate was added and the mixture was cooled to room temperature. 30 g of talc was dispersed in the batch.

The obtained spray suspension was applied on placebo tablets as described in Example 4. The polymer application corresponded to 4 mg/cm². The spraying time was 62 minutes. Then 40 g of an 18.7% aqueous talc suspension was additionally sprayed on within 5 minutes. The tablets were dried for 2.5 hours at 40° C. in the drying oven. The tablets had a uniform, glossy coating. In the disintegration test per the European Pharmacopoeia, they exhibited the following values in demineralized water and synthetic gastric fluid:

|  | Polymer application | | |
| --- | --- | --- | --- |
| Medium | 2 mg/cm² | 4 mg/cm² | uncoated |
| Demineralized water | 2 to 2.5 min | 3.7 to 6 min | 1 to 13 sec |
| 0.1 N HCl | 1 to 1.3 min | 1 to 1.5 min | 1 to 13 sec |

9. Colored Masking Coating with an Ionic Emulsifier and a Lipophilic Plasticizer In a glass beaker there were mixed, for 3 minutes, 370 g of demineralized water, 4.2 g of sodium lauryl sulfate and 9 g of dibutyl sebacate and united slowly under stirring with 60 g of a copolymer of methyl methacrylate, butyl methacrylate and dimethylaminoethyl methacrylate in proportions of 25:25:50 (mean particle size 15.3 $\mu$m) then stirred for 3.5 hours at room temperature. To this suspension there was added 100 g of 20% talc suspension and the contents were mixed uniformly.

The obtained spray suspension was applied on placebo tablets as described in Example 4. The polymer application corresponded to 4 mg/cm². The spraying time was 95 minutes. Then 55 g of pigment suspension (comprising 0.2% Polysorbate 80, 14.9% talc, 2.1% magnesium stearate, 6.4% titanium dioxide, 6.4% quinoline yellow, 2.1% polyethylene glycol 6000 and 67.9% water) was sprayed on within 15 minutes. The tablets were dried overnight at room temperature. They had a smooth, glossy coating. In the disintegration test per the European Pharmacopoeia, they exhibited the following values in demineralized water and synthetic gastric fluid:

| Medium | Polymer application | | |
|---|---|---|---|
| | 2 mg/cm² | 4 mg/cm² | uncoated |
| Demineralized water | 4.5 to 9.4 min | 7.4 to >20 min | 1 to 13 sec |
| 0.1 N HCl | 0.5 to 1.0 min | 1.0 to 1.1 min | 1 to 13 sec |

10. Colored Masking Coating with a Nonionic Emulsifier and a Hydrophilic Plasticizer In a glass beaker there were premixed, by means of a paddle stirrer, 333.5 g of demineralized water, 12.6 g of 33.3% Polysorbate 80 solution and 9 g of triethyl citrate, and 60 g of a copolymer of methyl methacrylate, butyl methacrylate and dimethylaminoethyl methacrylate in proportions of 25:25:50 (mean particle size 15.3 µm) was slowly stirred in then stirred for 1.5 hours at room temperature. Then there was added 50 g of 10% talc suspension, the contents were homogenized for 10 minutes at 3000 rpm with the Ultra Turrax and mixed with 2 to 3 drops of anti-foaming emulsion on the magnetic stirrer.

The obtained spray suspension was applied on placebo tablets as described in Example 4. The polymer application corresponded to 4 mg/cm². The spraying time was 70 minutes. Then 55 g of pigment suspension (according to Example 9) was sprayed on within 15 minutes. Half of the tablets were dried overnight at room temperature, while the other half were dried for 6 hours at 40° C. in the drying oven. The tablets had a smooth, glossy coating. In the disintegration test per the European Pharmacopoeia, they exhibited the following values in demineralized water and synthetic gastric fluid:

| Medium | Polymer application 4 mg/cm² | | |
|---|---|---|---|
| | Drying at room temperature | Drying at 40° C. | uncoated |
| Demineralized water | 3.2 to 5.5 min | 1.5 to 7.1 min | 1 to 13 sec |
| 0.1 N HCl | 0.7.0 to 1.0 min | 0.7 to 1.0 min | sec |

11. Colored Masking Coating with a Nonionic Emulsifier and a Hydrophilic Plasticizer In a glass beaker there were mixed 175 g of demineralized water, 18 g of 33.3% Polysorbate 80 solution and 9 g of triethyl citrate at room temperature. Then 60 g of a copolymer of methyl methacrylate, butyl methacrylate and dimethylaminoethyl methacrylate in proportions of 25:25:50 (mean particle size 15.3 µm) was slowly added thereto and stirred overnight. Then there was added thereto 40 g of 3% glycerol monostearate suspension, the contents were homogenized for 10 minutes at a speed of 3000 rpm with the Ultra Turrax, diluted with water to 400 g and mixed with 2 drops of anti-foaming emulsion.

The obtained spray suspension was applied on placebo tablets as described in Example 4. The polymer application corresponded to 4 mg/cm². The spraying time was 56 minutes. After application, 25 g of 3% GMS suspension was sprayed on within 5 minutes. In order to obtain a colored coating, 35 g of pigment suspension (comprising 0.2% polyethylene glycol 6000, 2.4% GMS, 2.4% titanium dioxide, 2.4% quinoline yellow and 92.6% water) was additionally sprayed on within 8 minutes. Half of the tablets were dried overnight at room temperature, while the other half were dried for 6 hours at 40° C. in the drying oven. They had a smooth, uniformly colored coating. In the disintegration test per the European Pharmacopoeia, they exhibited the following values in demineralized water and synthetic gastric fluid:

| Medium | Polymer application | | | |
|---|---|---|---|---|
| | 3 mg/cm² Drying at room temperature | 4 mg/cm² Drying at room temperature | 4 mg/cm² Drying at 40° C. | uncoated |
| Demineralized water | 2.4 to 6.4 min | 15 to >20 min | 6.3 to >20 min | 1 to 13 sec |
| 0.1 N HCl | 0.3 to 0.6 min | 0.5 to 0.75 min | 28 to 45 sec | 1 to 13 sec |

12. Powder Coating with Subsequent Transformation to Film by Infrared Radiation

In a glass beaker there were mixed 85.0 g of demineralized water, 9 g of 33.3% Polysorbate 80 solution, 6 g of ATBC, then 30 g of a copolymer of methyl methacrylate, butyl methacrylate and dimethylaminoethyl methacrylate in proportions of 25:25:50 (mean particle size 15.3 µm) was suspended therein and stirred for one hour.

The obtained polymer suspension was applied in a layer of 500 µm thickness on a glass plate by means of a doctor blade and was transformed to a film by heating to 80° C. for 5 minutes under an infrared lamp. There was obtained a clear glossy film that did not dissolve in water.

13. Powder Coating with Subsequent Transformation to Film by Infrared Radiation

In a glass beaker there were mixed 81.5 g of demineralized water, 9 g of 33.3% aqueous Polysorbate 80 solution, 4.5 g of TEC, then 30 g of a copolymer of methyl methacrylate, butyl methacrylate and dimethylaminoethyl methacrylate in proportions of 25:25:50 (mean particle size 15.3 µm) was suspended therein and stirred for 1 hour. The obtained polymer suspension was applied as a layer and transformed to a film as in Example 12. There was obtained a clear film that did not dissolve in water.

14. Powder Coating with Subsequent Transformation to Film by Microwaves

A polymer suspension according to Example 12 was applied as described therein and was transformed to a film in a NE-972-973 microwave combination apparatus (Panasonic Co.) by treatment for 12 minutes at 360 W. There was obtained a clear glossy film that did not dissolve in water.

15. Powder Coating with Subsequent Transformation to Film by Microwaves

A polymer suspension according to Example 13 was applied as described therein and transformed to a film as in Example 14. There was obtained a clear, flexible and glossy film that did not dissolve in water.

16. Taste-masking Coating

The experiment described in Example 4 was repeated with quinidine sulfate tablets. A sensory test yielded the following times for masking of the bitter taste.

|  | Polymer application | | | |
|---|---|---|---|---|
|  | 1 mg/cm² | 2 mg/cm² | 4 mg/cm² | uncoated |
| Masking of taste | 20 sec | 5 min | 10 min | 1 to 13 sec |

17. Coating for Insulation Against Moisture

In an MZ 50 colloid mill (Fryma Co.) there were dispersed for 1.5 hours 1540 g of demineralized water, 400.0 g of a copolymer of methyl methacrylate, butyl methacrylate and dimethylaminoethyl methacrylate in proportions of 25:25:50 (mean particle size 15.3 μm), 20.0 g of sodium lauryl sulfate and 40.0 g of dibutyl sebacate.

In 388.0 g of this suspension there were dispersed 34.0 g of talc and 433.0 g of demineralized water, after which stirring was continued for a further 10 minutes.

The obtained spray suspension was applied on Methylene Blue tablets as described in Example 4. The total polymer application corresponded to 4 mg/cm². The spraying time was 110 minutes. Then the product was dried for 4 hours in the drying oven at 40° C. The tablets had a glossy uniform coating and, in the disintegration test per the European Pharmacopoeia, exhibited the values listed in the table in demineralized water and synthetic gastric fluid. In addition, the times for penetration of the test liquid through the film coating into the tablet core were determined by the appearance of a blue coloration.

|  | Polymer application | | | |
|---|---|---|---|---|
|  | 1 mg/cm² | 2 mg/cm² | 4 mg/cm² | uncoated |
| Disintegration in demineralized water | 0.3 to 1.5 min | 15 to >20 min | >20 min | <1 min |
| Disintegration in 0.1 N HCl | 16 to 18 sec | 20 to 32 sec | 40 to 52 sec | 10 to 37 sec |
| Decomposition in gastric fluid, pH 6.8 | 40 sec | 1 to 2 min | 2.5 to 7.5 min | <1 min |

|  | Polymer application | | | |
|---|---|---|---|---|
|  | 1 mg/cm² | 2 mg/cm² | 4 mg/cm² | uncoated |
| Penetration of water | not determined | >10 min | >20 min | immediate |

18. Masking Coating with Particle Size that is not in Conformity with the Invention The experiment described in Example 4 was repeated with coarser copolymer of methyl methacrylate, butyl methacrylate and dimethylaminoethyl methacrylate in proportions of 25:25:50 (mean particle size 42 μm). The spray application proceeded irregularly because of intense dust formation. The coating was not uniform and had a rough, irregular surface.

19. Masking Coating without Plasticizer Addition

The experiment described in Example 4 was repeated without addition of TEC. The spray application proceeded irregularly because of intense dust formation. The coating was not uniform and had a rough, irregular surface.

20. Masking Coating without Surfactant Addition

The experiment described in Example 4 was repeated without addition of Polysorbate 80 solution. The spray application proceeded irregularly because of intense dust formation. The coating was not uniform and had a rough, irregular surface.

What is claimed is:

1. A powder consisting of a copolymer of units consisting of radical-polymerized C1 to C4 alkyl esters of acrylic or methacrylic acid and further (meth)acrylate monomers with functional tertiary amino groups the content of the polymerized monomers with functional tertiary amino groups being between 30 and 70% of the copolymer, characterized in that the powder has a mean particle size 1 to 40 μm as measured by laser refraction in highly diluted medium.

2. A powder consisting of a copolymer of radical-polymerized monomers consisting of 20 to 30 wt % of methyl methacrylate, 20 to 30 wt % of butyl methacrylate and 60 to 40 wt % of dimethylaminoethyl methacrylate, the powder having a mean particle size of 1–40 μm as measured by laser refraction in highly diluted medium.

* * * * *